United States Patent [19]
Filipi et al.

[11] Patent Number: 5,813,976
[45] Date of Patent: Sep. 29, 1998

[54] STABILIZING INSTRUMENTATION FOR THE PERFORMING OF ENDOSCOPIC SURGICAL PROCEDURES

[76] Inventors: Charles J. Filipi, 1328 N. 127th Ave., Omaha, Nebr. 68154; Douglas A. Cornet, 3007 Frederick St., Omaha, Nebr. 68105

[21] Appl. No.: 627,731

[22] Filed: Apr. 2, 1996

[51] Int. Cl.⁶ .................................................. A61B 1/00
[52] U.S. Cl. ........................................ 600/102; 600/114
[58] Field of Search ................................ 600/101, 102, 600/104, 106, 114, 117, 146; 604/174, 184, 179, 180, 264; 606/1, 130, 108, 78

[56] References Cited

U.S. PATENT DOCUMENTS

| 3,557,780 | 1/1971 | Sato ............................................. 128/4 |
| 4,108,211 | 8/1978 | Tanaka ...................................... 138/120 |
| 4,290,421 | 9/1981 | Siegmund ................................... 128/6 |
| 4,593,681 | 6/1986 | Soni ........................................ 600/102 |
| 4,633,865 | 1/1987 | Hengstberger et al. ............ 600/114 X |
| 4,686,965 | 8/1987 | Bonnet et al. ...................... 600/114 X |
| 4,759,348 | 7/1988 | Cawood ...................................... 128/6 |
| 4,794,912 | 1/1989 | Lia .............................................. 128/4 |
| 4,941,454 | 7/1990 | Wood et al. ................................ 128/4 |
| 4,962,751 | 10/1990 | Krauter ...................................... 128/4 |
| 4,972,827 | 11/1990 | Kishi et al. ......................... 600/114 X |
| 5,014,515 | 5/1991 | Krauter ...................................... 60/581 |
| 5,025,778 | 6/1991 | Silverstein et al. ......................... 128/4 |
| 5,167,627 | 12/1992 | Clegg et al. ............................. 604/101 |
| 5,184,601 | 2/1993 | Putman ....................................... 128/4 |
| 5,297,536 | 3/1994 | Wilk ............................................. 128/4 |
| 5,299,562 | 4/1994 | Heckele et al. ............................. 128/4 |
| 5,331,948 | 7/1994 | Utsumi et al. .............................. 128/4 |
| 5,337,732 | 8/1994 | Grundfest et al. .......................... 128/4 |
| 5,351,676 | 10/1994 | Putman ....................................... 128/4 |
| 5,375,588 | 12/1994 | Yoon ........................................... 128/4 |
| 5,429,598 | 7/1995 | Waxman et al. .......................... 604/51 |
| 5,540,648 | 7/1996 | Yoon ................................... 600/102 X |

FOREIGN PATENT DOCUMENTS 5-115423  5/1993  Japan ..................................... 600/102

*Primary Examiner*—Beverly M. Flanagan
*Attorney, Agent, or Firm*—Woodard, Emhardt, Naughton Moriarty & McNett

[57] ABSTRACT

Apparatus and methods are disclosed for percutaneously providing a stabilized platform for performing endoscopic surgery. The disclosed instrumentation includes an endoscope, a fixation catheter, a loop suture, and a rigid mount. A loop end of the loop suture is inserted into the gastrointestinal lumen through the fixation catheter and encompasses the endoscope positioned within the gastrointestinal lumen. The thread end of the loop suture remains external of the patient and is tautly connected to the rigid mount to provide the desired stability to the endoscope for the performance of an endo-surgical operation. Distal to the stabilizing assembly, the endoscope has articulated joints for positioning the distal end of the endoscope in close proximity to the surgical site, and includes manipulator arms which extend beyond the distal face of the endoscope to facilitate access to the surgical site.

19 Claims, 13 Drawing Sheets

STABILIZING INSTRUMENTATION FOR THE PERFORMING OF ENDOSCOPIC SURGICAL PROCEDURES

FIELD OF THE INVENTION

This invention relates to apparatus and methods for performing precise surgical procedures within a gastrointestinal lumen.

BACKGROUND OF THE INVENTION

In all forms of mini-access surgery, an operator platform and instrument fulcrums are important for the performance of precise tissue manipulation and incision. A stable operating environment is particularly important for intra-luminal surgery; that is, surgery accomplished with an endoscope inserted through a natural body orifice such as the mouth or anus. The standard locking mechanism used in the currently available endoscopes provides only a minimum amount of resistance which is inadequate to serve as the requisite stable platform for precise endoscopic surgery. Some stabilization can be provided by pushing the side of the endoscope against the body conduit or gastrointestinal wall, but this technique does not adequately allow a surgeon to manipulate the tissue of an internal body lumen to perform precise surgical procedures. A stable platform is essential for intra-luminal surgery using an endoscope because, without it, the risks of inadvertent perforation, uncontrolled bleeding, and unacceptable surgical margins are high. U.S Pat. Nos. 5,184,601 and 5,351,676 to Putnam disclose a surgical support apparatus for supporting a rigid surgical instrument, such as an endoscope, at a desired viewing position and orientation within a body cavity. This support apparatus may be mounted on a portable console and maintains the instrument in a set position. A disadvantage of this support apparatus is that, in order for the surgical instrument to be fixed relative to the console or operating environment, it must be rigid; therefore, it must be surgically inserted into the body cavity. Consequently, such a support apparatus could not be used to provide the necessary internal fixation point for a flexible endoscope that has been inserted through a natural body orifice.

In addition to the problem of providing an internal fixation point for a flexible endoscope, the flexibility of the endoscope and the remoteness of its working end within the body cavity from the surgeon's manipulations outside the body greatly diminish the surgeon's sense of the position, orientation, and movement of the endoscope. Without tactile feedback, the surgeon must rely almost solely upon endoscopic observation in performing the surgical manipulations.

U.S. Pat. No. 4,759,348 to Cawood discloses a surgical instrument attached to a flexible endoscope assembly directed to the removal of kidney stones through an incision in the renal pelvis. The surgical instrument takes the form of a version of forceps, can be held and operated by one hand, and is rigid enough to provide the surgeon with tactile feedback. Meanwhile the optical head of the endoscope provides the surgeon with visual confirmation of his manipulation with the surgical instrument. The rigidity of the forceps manipulator limits the region of the body cavity to which access can be gained. In the performance of intra-luminal surgical operations unhindered by the limited access afforded by the insertion of a rigid instrument to guide a flexible endoscope, instrument rigidity, greater than that currently available in endoscopes known in the prior art, is needed in order to provide a surgeon with the requisite internal fixation point that will enable him to accomplish intra-luminal surgery involving such operations as grasping, cutting, suturing, and coagulating of tissue.

Articulated control of the distal end of the endoscope is essential in order to locate the working end of the endoscope in close proximity to the surgical site. Conventional methods of controlling a flexible endoscope are disclosed in such references as U.S. Pat. No. 3,557,780 to Sato and U.S. Pat. No. 4,108,211 to Tanaka, both of which describe control methods using wires or cables. Additionally, U.S. Pat. No. 5,337,732 to Grundfest et al. discloses a method for orienting the plurality of segments of an endoscope using a compressed gas control means. The devices shown in these references may be able to orient the distal end of an endoscope in the desired location proximate to the surgical site; however, they may not provide sufficient stability to permit the surgeon to execute the requisite tissue manipulation and excision. Forces exerted on the endoscope during surgery could cause the endoscope to move out of position. For example, the wires and cables used by Sato and by Tanaka are unable to resist compressive forces; thus, a compressive force applied to the distal end of the endoscope will re-orient the flexible endoscope. Similarly, the endoscope disclosed by Grundfest et al., having gas-actuated segments separated by bellows, may not be able to adequately counteract forces exerted on the endoscope. Hence, these conventional methods known by those skilled in the art may provide insufficient rigidity to resist re-orientation of the endoscope under the applied loads of surgical operations.

SUMMARY OF THE INVENTION

An object of the present invention therefore lies in providing a stabilized surgical endoscope for the performing of precise endoscopic surgical procedures. To this end, a rigid stabilizing assembly is described that remains rigid under applied loads in any direction and of a magnitude commensurate with that required for intra-luminal endoscopic surgery and, therefore, provides the surgeon with the stable platform necessary for the cutting, coagulating, grasping, and excising of tissue. A further object is to provide a stabilizing mechanism that is percutaneously mounted so that the endoscope is held fixed relative to the operating environment and gastrointestinal lumen by a stabilizing assembly that passes through the skin, abdominal wall, and wall of the gastrointestinal lumen into which the endoscope has been positioned. As used herein, the term gastrointestinal lumen denotes lumen in the abdominal cavity, such as the gastric or colonic lumen, into which an endoscope can be inserted through a natural orifice, such as the mouth or anus. A still further object of the present invention is to provide a method for percutaneously stabilizing an endoscope inserted into a gastrointestinal lumen.

In brief, a stabilizing assembly according to the present invention includes a fixation catheter passing through the skin, abdominal wall, and wall of the gastrointestinal lumen; a loop suture inserted through the fixation catheter and into the gastrointestinal lumen; and a rigid mount to which the loop suture is tied and which is fixed with respect to the operating environment, such as the operating table. The fixation catheter includes a skin bolster that contacts the rigid mount, as well as a catheter portion that penetrates the skin, abdominal wall, and wall of the gastrointestinal lumen into which the endoscope has been inserted. The loop suture includes a loop end and two thread ends. The loop end passes through the catheter lumen of the fixation catheter and forms a loop in the gastrointestinal lumen. This loop then engages a short rigid section on an otherwise flexible endoscope. The thread ends of the loop suture are tautly connected to the rigid mount. The rigid mount, in turn, contacts the skin bolster of the fixation catheter with such a normal force that lateral forces exerted on the rigid mount by the endoscope and transmitted through the loop suture do not overcome the frictional force between the skin bolster and the rigid mount. In this manner, the stabilizing assembly provides a stable platform to which an endoscope position in a gastrointestinal lumen can be mounted and held fixed. More than one stabilizing assembly may be utilized to anchor the endoscope for intra-luminal surgery.

As disclosed herein, according to one embodiment of the present invention, an endoscope has a rigid section with a series of grooves or valleys therein extending circumferentially around the endoscope in order to provide a stable position into which the loop suture can locate. Additionally, location of the loop suture in such a groove inhibits the loop suture from frictionally engaging the tip of the catheter, thereby reducing wear on the loop suture. Moreover, to prevent the loop suture from digging into any tissue of the gastrointestinal lumen that might be exposed near the tip of the catheter, a flexible collar is slideably mounted on the loop suture and contains the suture near the catheter tip. In order to secure the skin bolster of the fixation catheter to the patient's body, the skin bolster may have holes spaced around its periphery or an outer rim of flexible plastic through which sutures can be placed to attach the skin bolster to the skin.

The distal end of the endoscope must be maneuverable in order to position it in close proximity to the surgical site. Articulation of the endoscope is achieved by controlling the tension in control wires that run through the endoscope to a proximal joint and a distal joint, both located within the gastrointestinal lumen and distal to the stabilizing assembly. The joints comprise an alternating sequence of extension segments and ball joints held together by a connecting cable. Control wires are utilized to obtain the desired shape of the endoscope. The endoscope is locked in the desired geometry by pressing the extension segments and ball joints together using the connecting cable. In an alternative embodiment, the endoscope comprises a series of integral extension segments, each having a protrusion on one end and a recess in the other end. The recess of one integral extension segment is sized to receive the protrusion of an adjacent integral extension segment. Control wires and a connecting cable are also utilized to articulate the endoscope made up of a series of integral extension segments.

To accomplish the desired intra-gastrointestinal surgical procedures, the endoscope contains several devices, such as an optical device, a suction or irrigation channel, and an instrument channel. Also, the endoscope has two manipulator arms located at its distal end. The manipulator arms extend beyond the distal end of the main body of the endoscope in order to facilitate access to the surgical site. Furthermore, the arms may include any number of surgical devices on their ends, and they may, in particular, include graspers capable of atraumatically grasping and manipulating the tissue of the wall of the gastrointestinal lumen. Means for controlling the flexible endoscope as well as the surgical instruments contained by the endoscope extend through the endoscope to its proximal end external to the patient where a handle containing the requisite readouts, controls, and sensors is located.

In a further aspect of the present invention, a method is disclosed for percutaneously stabilizing an endoscope inserted into a gastrointestinal lumen through a natural body orifice. The method includes the steps of inserting an endoscope into the gastrointestinal lumen, inflating the stomach, and inserting the catheter portion of a fixation catheter through the skin, abdominal wall, and wall of the gastrointestinal lumen. With the catheter portion so inserted the skin bolster of the fixation catheter rests on the surface of the skin adjacent the fixation point. The step of inserting the catheter portion includes making a small incision at the desired fixation point through the skin; inserting a needle in that incision; and advancing the fixation catheter over the needle until the catheter portion provides a passageway from exterior the patient to the gastrointestinal lumen. The method also includes the steps of removing the needle; advancing a loop suture through the catheter lumen until a loop having diameter great enough to receive the endoscope is formed in the gastrointestinal lumen; and snaring the endoscope with the loop suture. The snaring steps involves locating the rigid section of the endoscope and lassoing it with the loop end of the loop suture. The rigid section of the endoscope is located and the endoscope is passed through the loop end of the suture until the loop encircles the rigid section. The loop suture is pulled taut, thereby drawing the endoscope up against the tip of the catheter portion of the fixation catheter. The method further includes the steps of tautly securing the loop ends of the loop suture to a rigid mount and pressing the mount against the skin bolster of the fixation catheter. The rigid mount is fixed relative to the operating environment. Other features, objects, and advantages of the invention will become apparent from the following description.

DETAILED DESCRIPTION OF THE PREFERRED EMBODIMENT

Figure 1:
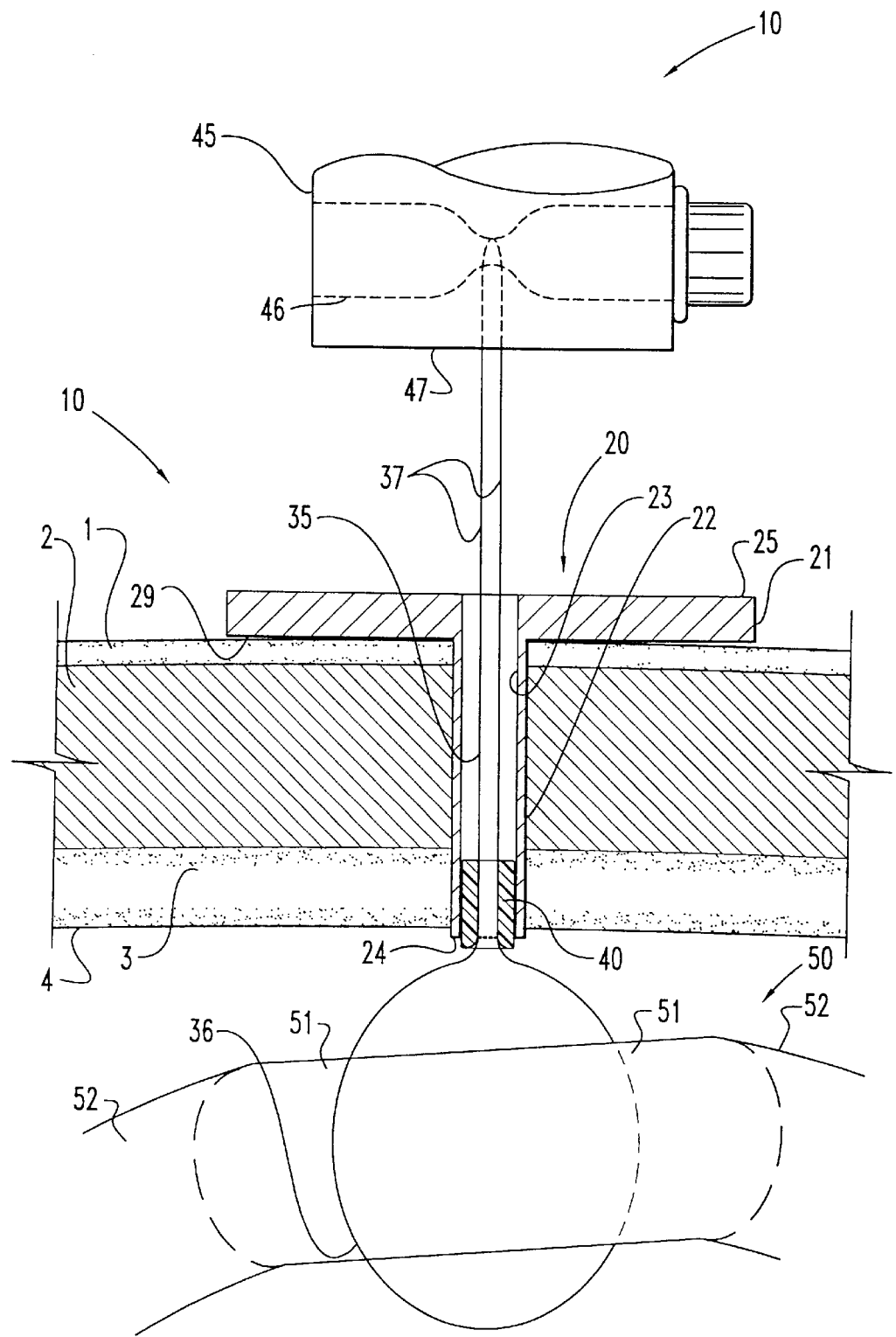
FIG. 1 is a partial side cross sectional view of the stabilizing assembly engaging an endoscope positioned within a gastrointestinal lumen.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, wherein identical numerals indicate the same elements throughout the figures, FIG. 1 illustrates stabilizing assembly 10 comprising fixation catheter 20, loop suture 35, and rigid mount 45. The fixation catheter 20 includes skin bolster 21 with lower surface 29 that rests on the surface of the patient's skin 1, as well as catheter portion 22 that penetrates skin 1, abdominal wall 2, and gastrointestinal lumen wall 3. Additionally, catheter lumen 23 extends through fixation catheter 20 from upper surface 25 of the skin bolster to tip 24 of catheter portion 22. Fixation catheter 20 may be made of a metal, such as steel, or other material, such as polyvinylchloride or silicone, so long as the material possesses sufficient rigidity such that it does not deform under the loads applied to fixation catheter 20 by rigid mount 45 and endoscope 50 during stabilization and use of endoscope 50 disposed within gastrointestinal lumen 4. Alternatively, the requisite rigidity could be supplied a reinforcing member, which may be placed into or about catheter portion 20 to support the fixation between endoscope 50 and rigid mount 45.

Figure 2:
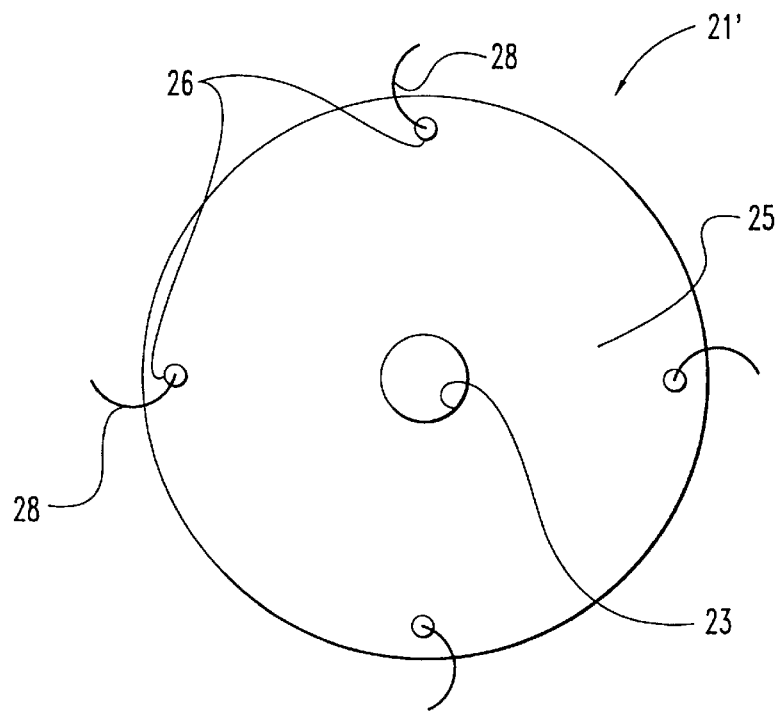
FIG. 2 is a top view of the fixation catheter according to one embodiment of the present invention illustrating holes used for securing the skin bolster to the skin.
Figure 3:
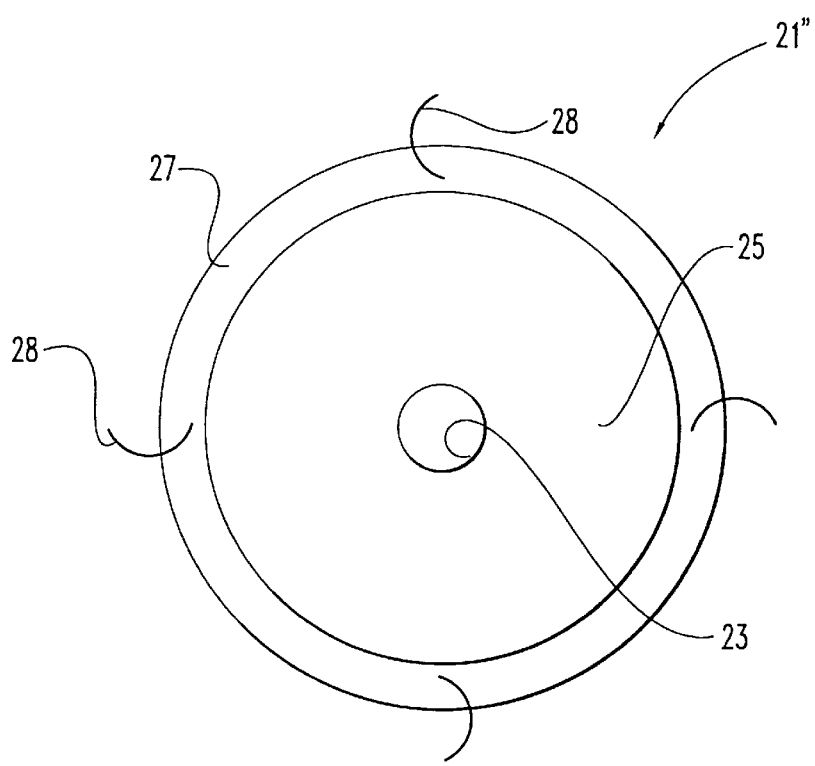
FIG. 3 is a top view of the fixation catheter according to an embodiment of the present invention illustrating a rim of plastic material for securing the skin bolster to the skin.

Securing skin bolster 21 to patient's skin 1 may be desirable to prevent displacement of skin bolster 21 during stabilization and operation of endoscope 50. FIGS. 2 and 3 show top views of skin bolster 21 with means for attachment to the skin. In FIG. 2, skin bolster 21' has four holes 26 extending from upper surface 25 of skin bolster 21' to lower surface 29 of the skin bolster. The number of holes 26 is not critical; however, they are preferably equally spaced about the perimeter of skin bolster 21'. Sutures 28 are then placed through holes 26 and into patient's skin 1 to retain skin bolster 21' in the desired location. FIG. 3 depicts skin bolster 21" having an outer rim 27 of flexible plastic, such as silicone, through which sutures 28 can be placed to attach skin bolster 21" to skin 1. In addition, each of skin bolsters 21' and 21" has substantially flat upper surface 25 for engaging substantially flat lower surface 47 of rigid mount 45.

The shape of the skin bolster 21, illustrated as circles in FIGS. 2 and 3, is not critical so long as upper surface 25 of skin bolster 21, has sufficient area for rigid mount 45 to contact.

Referring once again to FIG. 1, the means of connecting endoscope 50 to rigid mount 45 that is fixed with respect to the operating environment is loop suture 35. Loop suture 35 has self-opening loop end 36 disposed within gastrointestinal lumen 4 and encircling endoscope 50, as well as two thread ends 37. As illustrated in FIG. 1, loop suture 35 includes two thread ends 37 that extend through catheter lumen 23 and connect to rigid mount 45. Alternatively, on thread end 37 could be attached to the other so that only one thread end is connected to rigid mount 45. Loop suture 35 is preferably made of stainless steel or other material having suitable strength and resilient deformability, such as superelastic Nitinol wire. Loop suture 35 could also be constructed from a non-metal plastic material, provided the material is sufficiently strong and has sufficient resilient deformability. To prevent suture 35 from digging into the tissue of gastrointestinal lumen wall 3 exposed near tip 24 of fixation catheter 20, flexible collar 40 is slideably retained on loop suture 35. Flexible collar 40 has an inner lumen through which loop suture 35 passes and a diameter smaller than that of catheter lumen 23; hence, collar 40 rides on loop suture 35 just above endoscope 50. Collar 40 is made of a plastic such as polyurethane or polyvinylchloride, but could alternatively be constructed of metal or other material.

In order to stabilize endoscope 50 and provide an anchor resistant to lateral forces exerted on loop suture 35, rigid mount 45 presses against skin bolster 21 with such a normal force that lateral forces on rigid mount 45 do not overcome the frictional force between upper surface 25 of skin bolster 21 and lower surface 47 of rigid mount 45. Further, loop suture 35 is drawn taut to stabilize endoscope 50. Rigid mount 45 thus includes a means of drawing and retaining loop suture 35 taut, and thread ends 37 of loop suture 35 are connected to this means. In FIG. 1, this means is shown, by example, as ratcheting spool 46 which, when turned, takes up existing slack in loop suture 35 and retains it taut. Any of a variety of other mechanisms could be used as well. Also, it may be mentioned that the mechanism for drawing loop suture 35 taut could alternatively be placed in fixed position relative to rigid mount 45 rather than being directly mounted thereto.

As shown in FIG. 1, the endoscope 50 disposed within gastrointestinal lumen 4 includes rigid section 51 and flexible sections 52 both distal and proximal to rigid section 51. Loop end 36 of loop suture 35 encircles endoscope 50 at some location along rigid section 51. Rigid section 51 is provided on the otherwise flexible endoscope 50 so that the tightening of loop suture 35 about endoscope 50 does not cut into and damage endoscope 50. Rigid section 51 may have a smooth exterior comprising a stainless steel band disposed on endoscope 50; furthermore, rigid section 51 should preferably be no longer than 30 mm so that endoscope 50 can be passed down the throat of the patient without difficulty.

Figure 4:
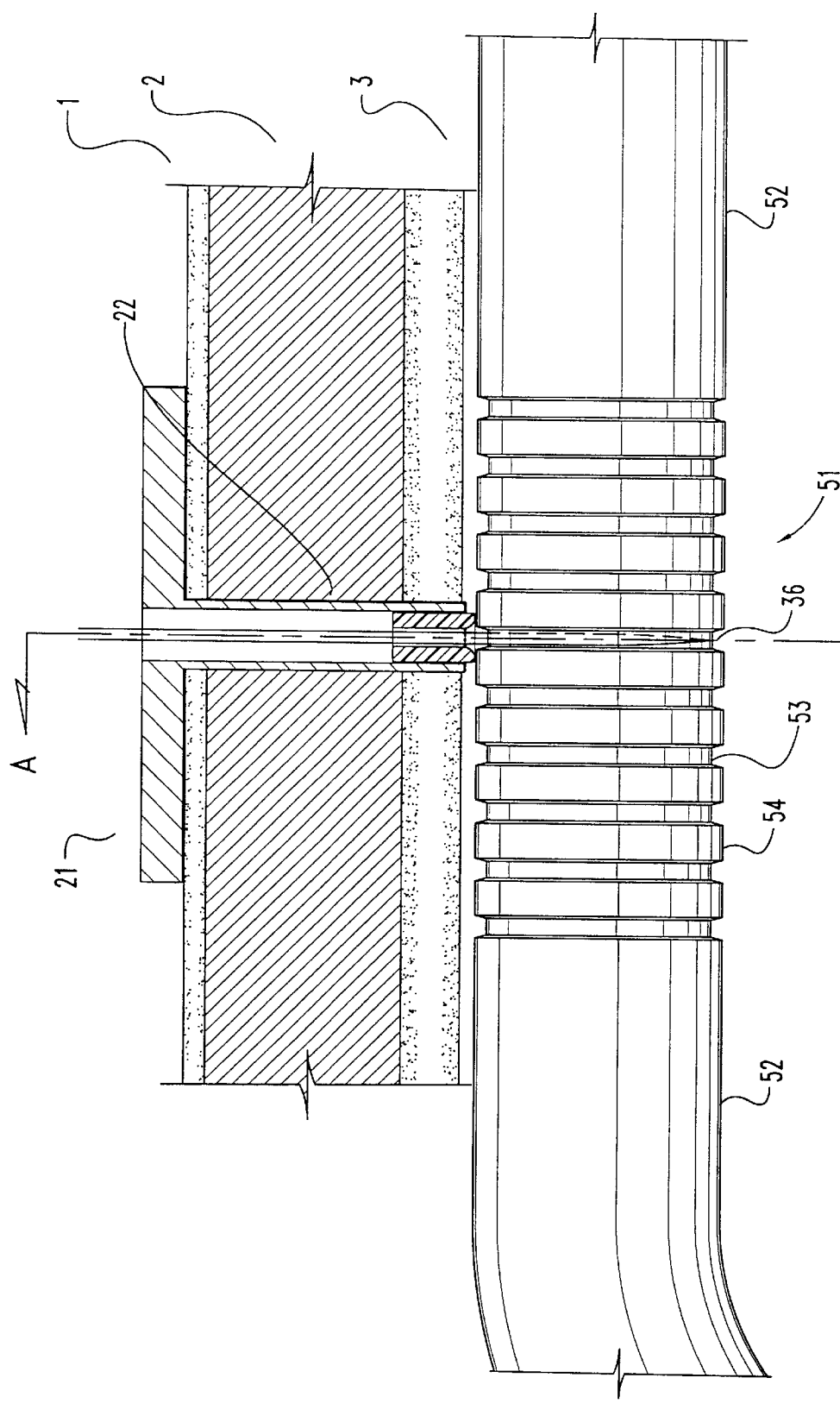
FIG. 4 is a partial side cross sectional view of the stabilizing assembly engaging an endoscope having grooves for receiving the loop suture.
Figure 4A:
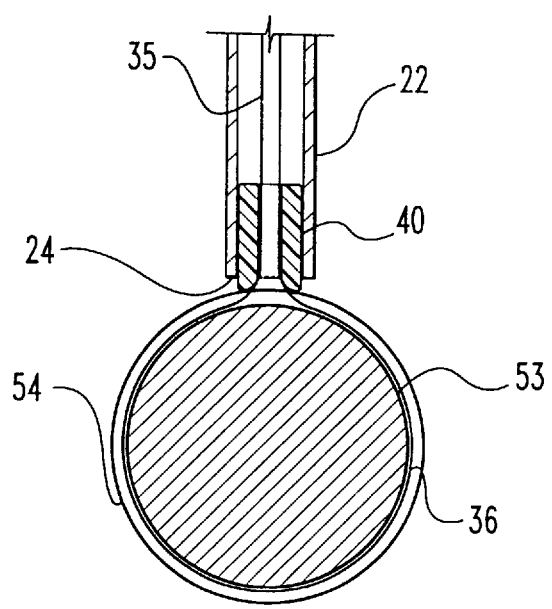
FIG. 4A is a cross sectional view taken along line A—A of FIG. 4.

FIG. 4 illustrates an embodiment of endoscope 50 in which rigid section 51 has a series of plateaus 54 separated by grooves 53. Plateaus 54 and grooves 53 extend circumferentially around endoscope 50. The purpose of grooves 53 is to provide a stable position into which loop end 36 of loop suture 35 can locate. The width of each groove 53 is smaller than the diameter of tip 24 of catheter portion 22 of fixation catheter 20 so that tip 24 preferably rests upon two adjacent plateaus 54. Thus, location of loop end 36 in a groove 53 between these two adjacent plateaus 54 inhibits loop suture 35 from frictionally engaging tip 24 of catheter portion 22. As seen from FIG. 4A, tip 24 of catheter portion 22 rests on plateau 54 while loop end 36 of loop suture 35 extends past tip 24 and into groove 53. Consequently, frictional wear of loop suture 35 against tip 24 of catheter portion 22 of fixation catheter 20 is reduced or eliminated. Plateaus 54 and grooves 53 of rigid section 51 of endoscope 50 may alternatively be rounded so as to create hills and valleys, respectively, to facilitate the stable positioning of loop end 36 within a valley.

Figure 5:
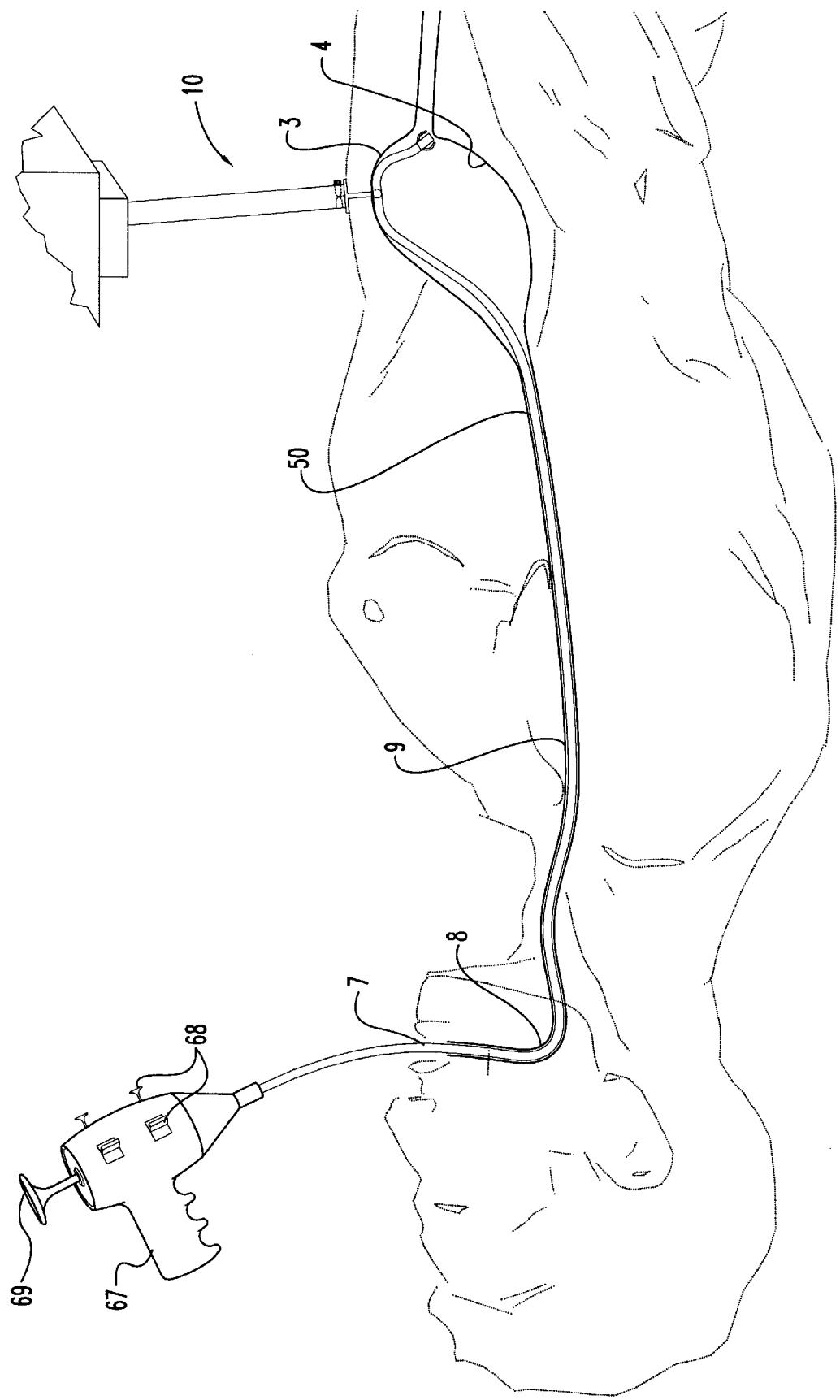
FIG. 5 is a schematic view showing the endoscope inserted into the gastrointestinal lumen and anchored by the stabilizing assembly.
Figure 6:
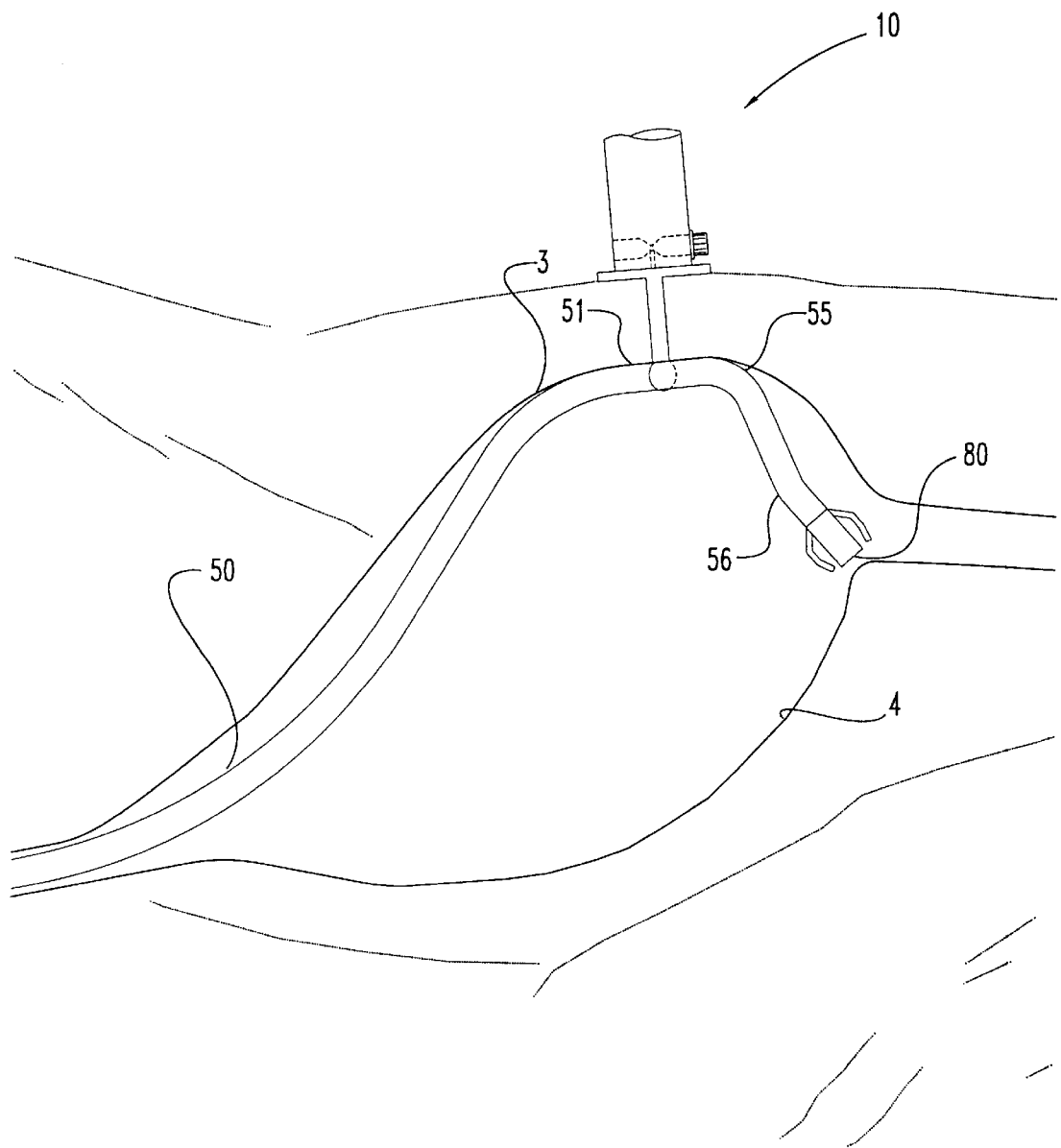
FIG. 6 is an enlargement of that portion of FIG. 5 showing the endoscope anchored within the gastrointestinal lumen by the stabilizing assembly.

FIG. 5 illustrates flexible endoscope 50 inserted through the patient's mouth 7, throat 8, and esophagus 9 and percutaneously stabilized in gastrointestinal lumen 4 by stabilizing assembly 10. An enlargement of that portion of FIG. 5 depicting the endoscope anchored within the gastrointestinal lumen by the stabilizing assembly is shown in FIG. 6. Distal to the anchor provided by stabilizing assembly 10, endoscope 50 has proximal joint 55 and distal joint 56 located distal to joint 55. Preferably, proximal joint 55 is configured to have a range of motion of +0°/−90° in one plane, and distal joint 56 has a range of motion of +110°/−90° in the same plane. Articulation of proximal joint 55 and distal joints 56 combined with rotation of endoscope 50 enables distal end 80 of endoscope 50 to have angle range of positioning angles for the performing of surgical procedures over various areas within gastrointestinal lumen 4.

Figure 7:
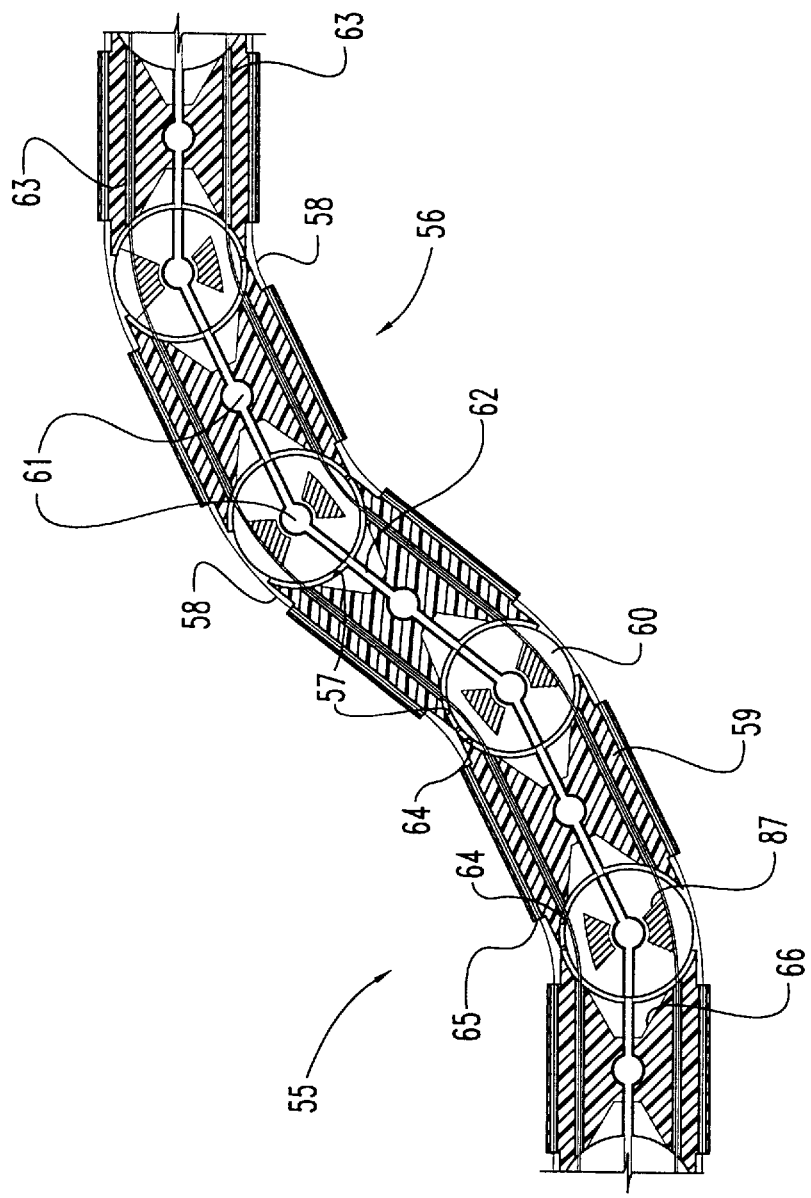
FIG. 7 is a cross sectional view of the endoscope core that houses the control structure of the endoscope according to one embodiment of the present invention.

FIG. 7 depicts a cross section of the endoscope core that houses the control structure for articulating the endoscope. The core structure shown in FIG. 7 is dimensioned to have a diameter of only about one quarter to one half that of the complete endoscope, thus allowing ample room within endoscope 50 for instrument channels, fiber optic cables, and mechanisms to control the surgical manipulations at distal end 80 of endoscope 50. Articulation of proximal joint 55 and distal joint 56 of flexible endoscope 50 is accomplished by controlling the tension in control wires 58. Joints 55 and 56 include a plurality of extension segments 59 separated by ball joints 60. The ends of each extension segment 59 have recesses 57 for receiving ball joints 60. Extension segments 59 and ball joints 60 have cavities 66 and 87, respectively, therein to allow connecting cable 62 to pass therethrough; further, cavities 66 and 87 are shaped to permit varied orientations of segments 59 and joints 60 without encumbering cable 62. Attachment mechanisms 61 connect extension segments 59 and ball joints 60 to connecting cable 62, and guide cables 63 maintain extension segments 59 and ball joints 60 in radial alignment. Adjacent ball joints 60, extension segments 59 have surfaces 64 made of a material having a high coefficient of friction, such as urethane. Also, wire guides 65 are attached to extension segments 59 and contain control wires 58. In the preferred embodiment, endoscope 50 has four control wires 58 spaced circumferentially 90° apart. Thus, tension created in one control wire 58 located on one side of endoscope 50 causes endoscope 50 to contract in that direction.

To articulate joints 55 and 56, the tension in control wires 58 is varied until endoscope 50 assumes the desired shape. To lock the endoscope in position, it is held in the desired geometry while extension segments 59 and ball joints 60 are pulled together using connecting cable 62. High coefficient of friction surfaces 64 of extension segments 59 seat against and retain ball joints 60. Disengagement of joints 55 and 56 is achieved by releasing tension in connecting cable 62 and allowing extension segments 59 and ball joints 60 to disengage. The means of articulating endoscope 50, by controlling the tension in control wires 58 and connecting cable 62, extends through endoscope 50 to its proximal end which is connected to handle 67, as shown in FIG. 5. Readouts, controls, and sensors, labeled generally as 68, in addition to port 69 for connection to a compressed gas source or insufflation machine (not shown) are provided on handle 67.

Figure 8:
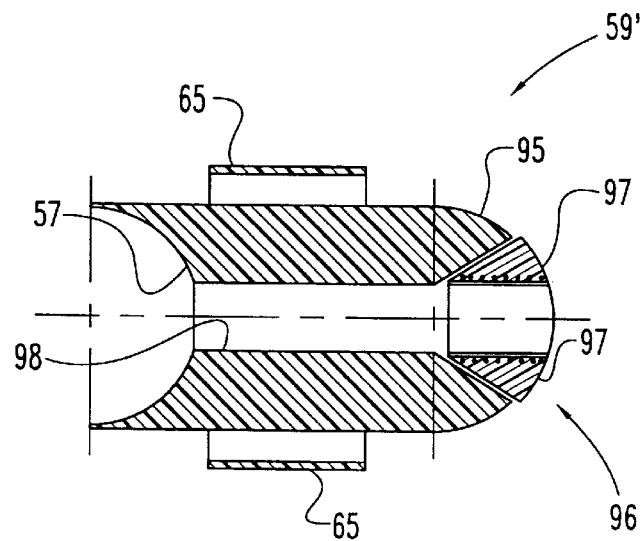
FIG. 8 is a cross sectional view of an integral extension segment of the control structure of the endoscope according to one embodiment of the present invention.

An alternative to distinct extension segments 59 and ball joints 60 is a universal joint member or the integral extension segment illustrated in FIG. 8. Integral extension segment 59' has protrusion 95 on one end and recess 57 in the other end. Protrusion 95 of one extension segment is sized to be received in recess 57 of an adjacent extension segment. Also, protrusion 95 includes a spring mounted nose 96 having an external surface 97 made of a material having a high coefficient of friction. Extension segment 59' has a passage 98 therethrough for receiving the connecting cable and also has wire guides 65 for containing the control wires. After adjusting the tension in the control wires to acquire the desired shape, the connecting cable is utilized to engage the extension segments 59' and to seat high friction coefficient surface 97 of nose 96 against the surface of recess 57 in an adjacent extension segment.

Figure 9:
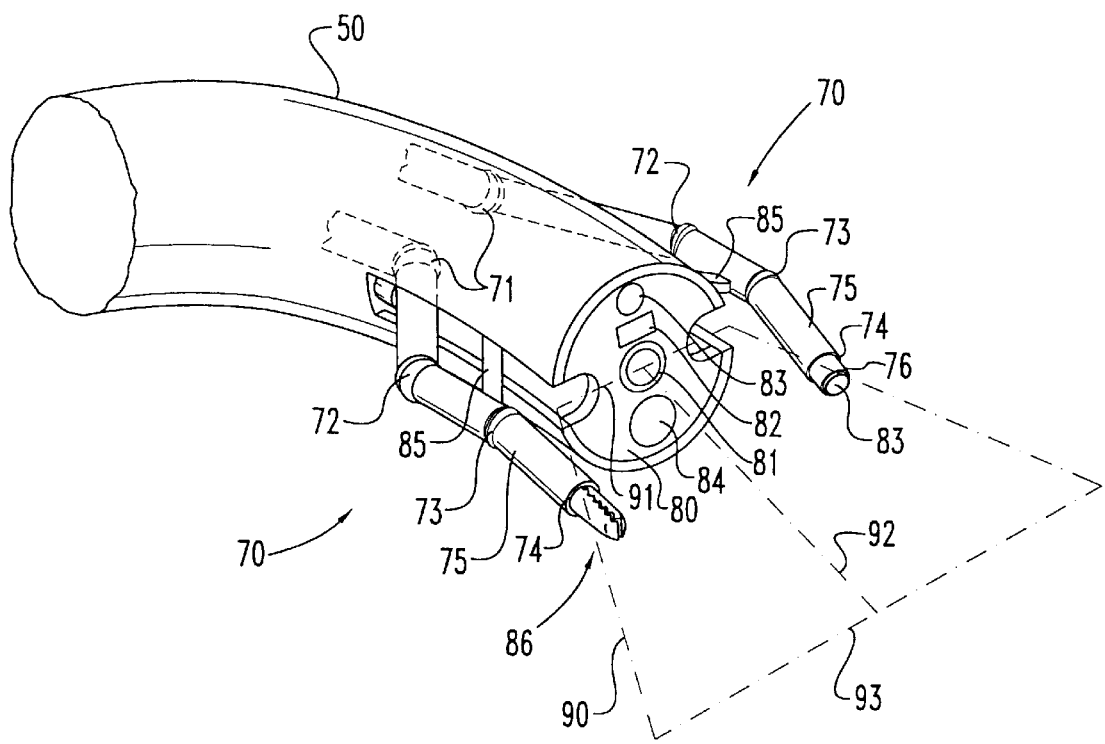
FIG. 9 is a perspective view of the distal end of the endoscope.
Figure 10:
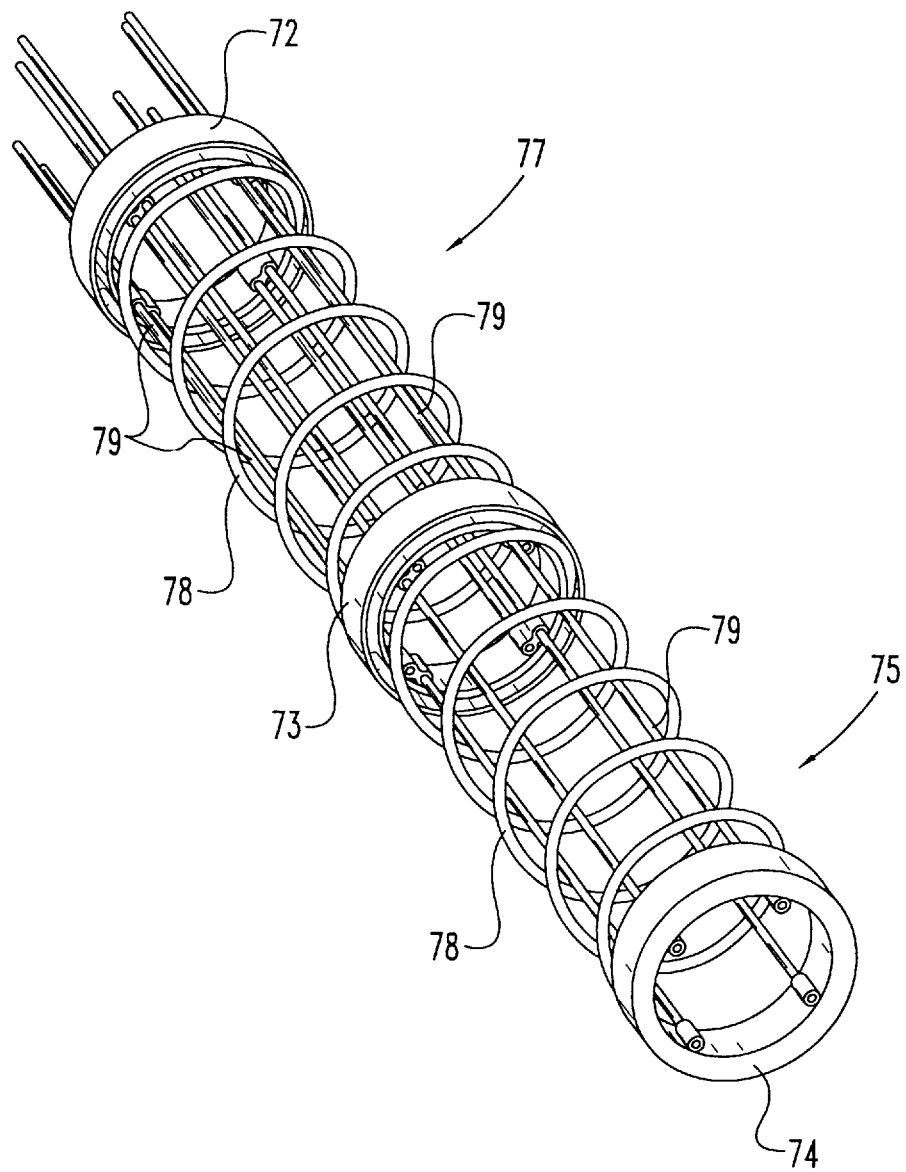
FIG. 10 is a perspective view according to one embodiment of the present invention illustrating a helical spiral means for extending the manipulator arm.

In order to perform a desired intra-gastrointestinal surgical operation, endoscope 50 may employ a plurality of surgical devices. For example, as shown in FIG. 9, endoscope 50 may include optical device 81, wash 82, suction/irrigation channel 83, or instrument channel 84. Additionally, proximate to distal end 80 of endoscope 50 are two manipulator arms 70. Using control means known in the art such as actuators 85, each arm 70 can be articulated about first joint 71 located within endoscope 50, second joint 72, or third joint 73 in order to position end 74 of third segment 75 in the desired location with respect to the surgical site on the wall of gastrointestinal lumen. Manipulator arms 70 include means for extending beyond the distal end 80 of the main body of endoscope 50. For example, third segment 75 may include telescopic portion 76 so that the reach of manipulator arm 70 is extended beyond distal end 80. Telescopic portion 76 may be housed within third segment 75 as shown in FIG. 9, or the extension of manipulator arm 70 may involve one or more segments of manipulator arm 70 that are elongated in a helical spiral. FIG. 10 depicts second segment 77 and third segment 75 of manipulator arm 70 comprising helical spirals 78 that can be elongated by the extension of rods 79 connected to manipulator arm 70 at second joint 72, third joint 73, end 74, and possibly helical spirals 78 themselves. As illustrated in FIG. 10, rods 79 are located in the interior of the manipulator arm 70; however, they could alternatively be connected to the exterior of arm 70.

Manipulator arms 70 may include any of the plurality of devices listed above, such as suction/irrigation channel 83 as depicted in FIG. 9. Moreover, grasper 86, capable of atraumatically grasping and manipulating the tissue of the wall of the gastrointestinal lumen, may be connected to end 74 of third segment 75 or, alternatively, to telescopic portion 76 of third segment 75. Grasper 86 is rotatably mounted in end 74 such that it is able to rotate ±180° about the longitudinal axis of third segment 75. The control of all devices located at distal end 80 of endoscope 50 is transmitted from handle 60 through endoscope 50 to its working end. Moreover, the control of instruments located on the ends of manipulator arms 70, such as grasper 86, further extends from endoscope 50 through manipulator arms 70 to the instruments.

A method for percutaneously stabilizing an endoscope in order to create the stable platform essential for intra-luminal surgery includes the step of inserting a flexible endoscope 50 into gastrointestinal lumen 4 through the patient's mouth 7, throat 8, and esophagus 9 as shown in FIG. 5. Endoscope 50 is preferably about 20 mm in diameter or smaller so that endoscope 50 can be easily passed through the patient's esophagus 9. For the same reason, rigid section 51 of endoscope 50 is preferably about 30 mm in length or less. Abdominal lumen 4 is inflated by passing a pressurized gas down endoscope 50 and into gastrointestinal lumen 4, thereby increasing the volume of gastrointestinal lumen 4 and providing an enlarged working area for the intra-luminal surgery.

Figure 11:
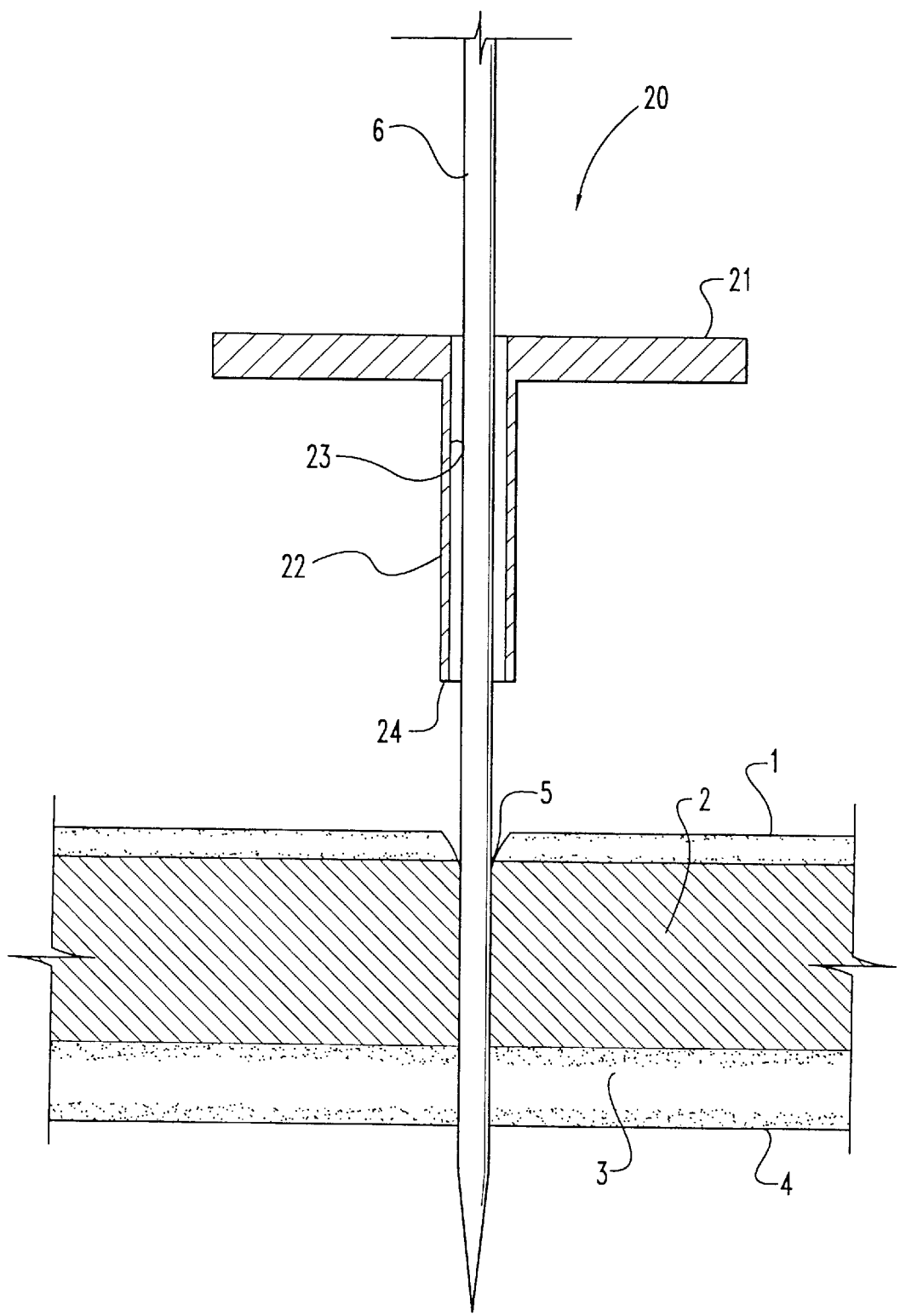
FIG. 11 is a partial side cross sectional view showing the step of advancing the fixation catheter over the needle.

Referring to FIG. 11, fixation point 5 through which stabilizing assembly 10 is percutaneously mounted is selected. When additional stabilization is desired or required, more than one fixation point 5 and accompanying stabilizing assembly 10 may be utilized so as to provide additional anchors for endoscope 50 disposed within gastrointestinal lumen 4. Fixation catheter 20 is inserted through skin 1, abdominal wall 2, and wall of the gastrointestinal lumen 3 by making a small incision through those structures at fixation point 5, inserting needle 6 through the incision and into gastrointestinal lumen 4, and advancing catheter lumen 23 of fixation catheter 20 over needle 6 until tip 24 of catheter portion 22 of the fixation catheter penetrates through the wall of gastrointestinal lumen 4. With fixation catheter 20 in place, needle 6 is removed in order to prevent damage to endoscope 50. Skin bolster 21 of fixation catheter 20 may be secured to the patient by suturing it to patient's skin 1 either through holes 26 as provided in skin bolster 21' illustrated in FIG. 2 or through outer ring 27 of needle pierceable material as provided on skin bolster 21" illustrated in FIG. 3.

Figure 12:
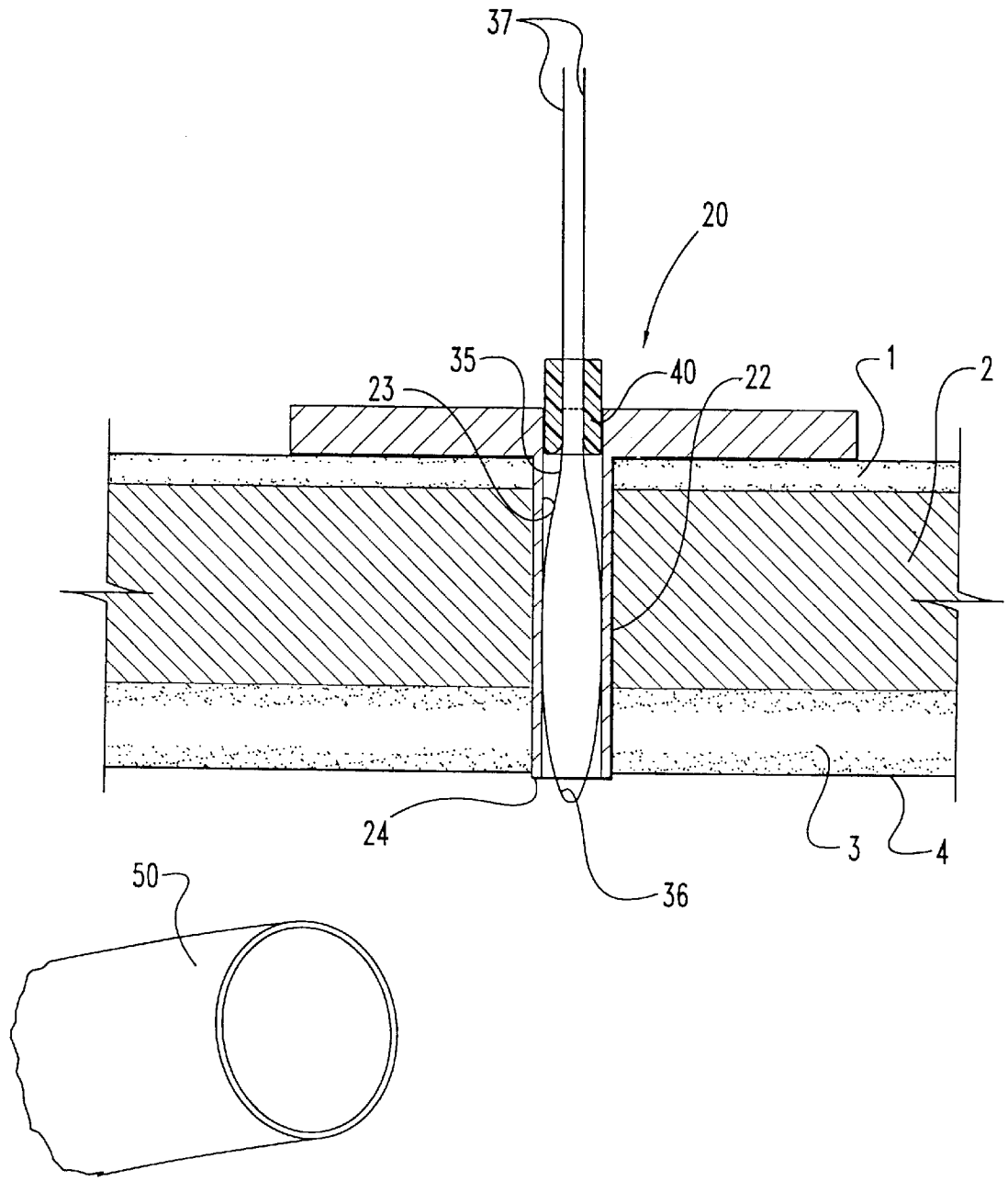
FIG. 12 is a partial side cross sectional view of the step of advancing the loop suture through the fixation catheter and into the gastrointestinal lumen.
Figure 13:
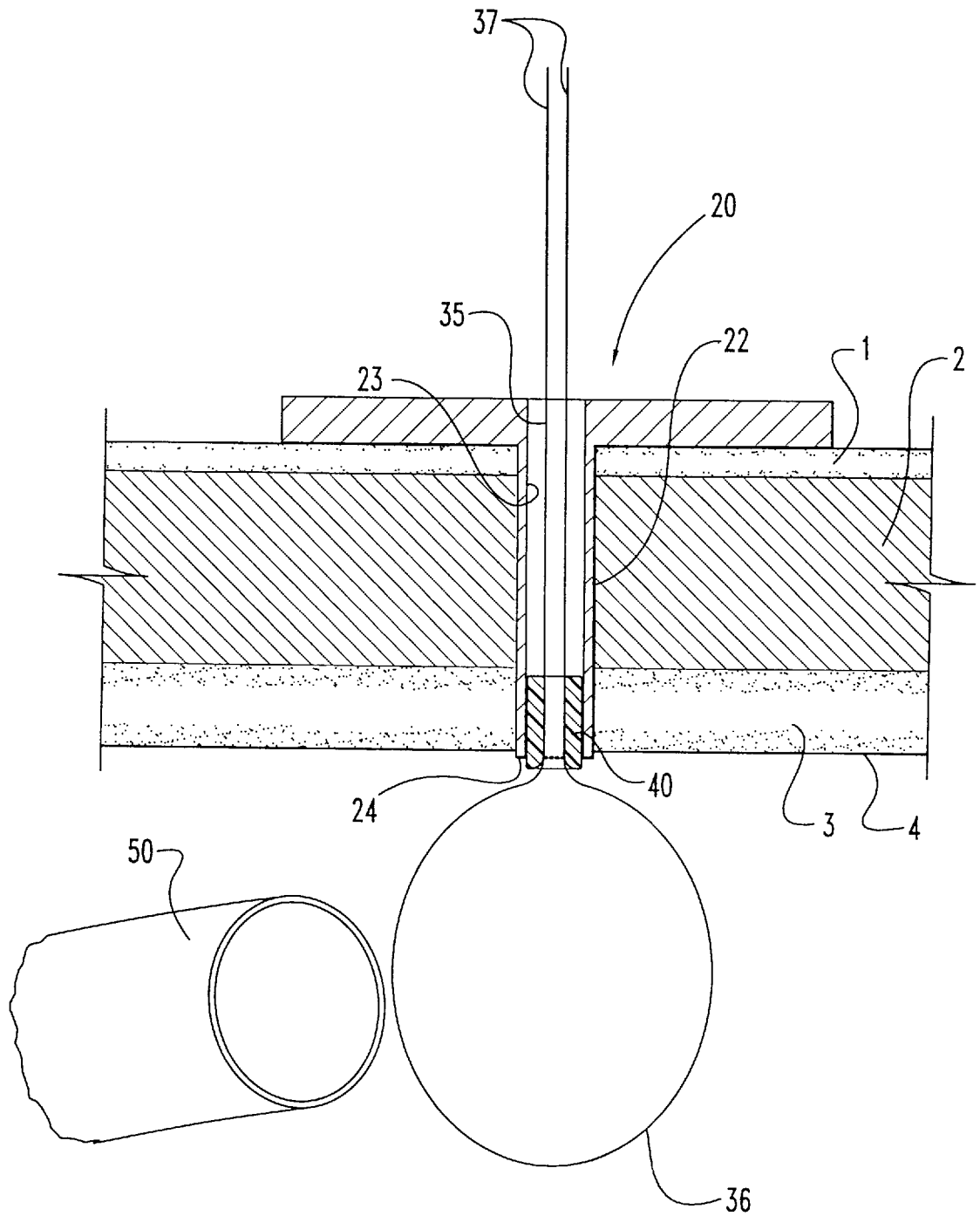
FIG. 13 is a partial side cross sectional view illustrating the loop suture deployed in the gastrointestinal lumen.

Illustrated in FIG. 12 is the step of advancing loop suture 35 through catheter lumen 23 until loop end 36 having a diameter great enough to receive endoscope 50 is formed in gastrointestinal lumen 4 as shown in FIG. 13. Either before or after advancing loop suture 35 through catheter lumen 23, flexible collar 40 may be provided on loop suture 35 in order to prevent loop suture 35 from cutting into the tissue of gastrointestinal lumen wall 3 in the area of catheter tip 24. Endoscope 50 is snared by loop suture 35 by lassoing rigid section 51 of endoscope 50 with loop end 36 of loop suture 35. This lassoing step further includes the steps of positioning rigid section 51 of the endoscope within loop end 36 by passing endoscope 50 through loop end 36 until it encircles rigid section 51 and enclosing loop end 36 of loop suture 35 around the circumference of the endoscope by pulling thread ends 37 of loop suture 35 directly outward away from fixation catheter 20. The snaring step is completed by further pulling thread ends 37 so as to draw rigid section 51 of endoscope 50 up against tip 24 of catheter portion 22 of fixation catheter 20.

Figure 14:
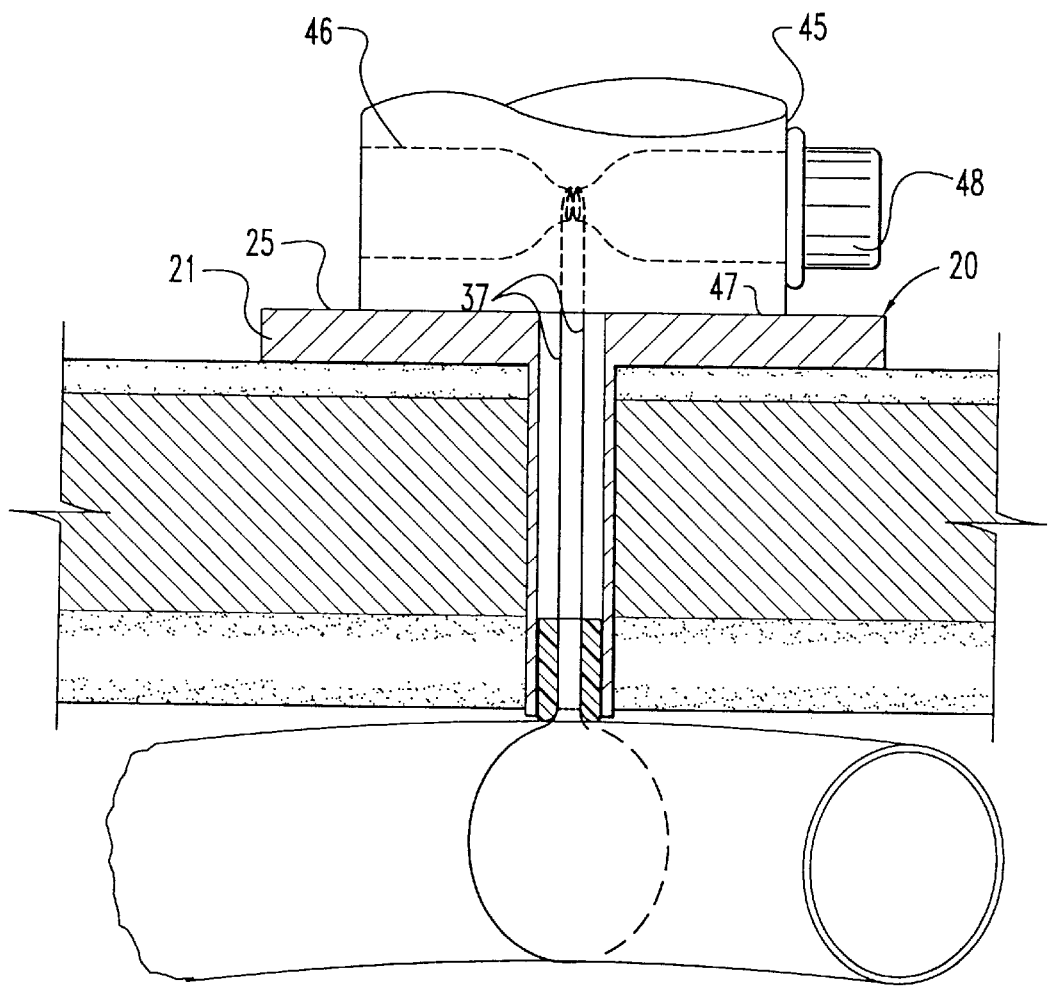
FIG. 14 is a partial side cross sectional view showing the steps of pressing the rigid mount against the skin bolster and drawing the loop suture taut to secure the endoscope.

In order to provide a means of keeping loop suture 35 drawn taut, thread ends 37 are connected to spool 46 of the rigid mount as shown in FIG. 14. Turning knob 48 of spool 46 wraps thread end 37 around the spool to thereby draw loop suture 35 taut. Rigid mount 45 presses against the skin bolster with such a force that lateral forces exerted on rigid mount 45 by endoscope 50 and transmitted through loop suture 35 do not overcome the frictional force between lower surface 47 of rigid mount 45 and upper surface 25 of skin bolster 21. To ensure against slippage, matching grooves and ridges could be placed on surfaces 25 and 47, or catheter 20 could be directly attached to rigid mount 45 by other means.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A stabilized endoscope assembly for the performing of endoscopic surgical procedures within a gastrointestinal lumen, said assembly comprising:

an endoscopic, said endoscope having a distal end portion disposed within the gastrointestinal lumen of a patient for the performing of an endoscopic surgical procedure therein;

a percutaneous fixation catheter, said percutaneous fixation catheter including a distal tip portion, a proximal portion, and a catheter portion therebetween, said catheter portion defining a percutaneous lumen extending from said distal tip towards said proximal portion, said fixation catheter being percutaneously placed with said distal tip portion extending into the gastrointestinal lumen and with said proximal portion positioned outside of the patient;

a rigid mount, said rigid mount being fixed with respect to the operating environment; and fixating means for fixedly attaching said endoscope relative to said rigid mount through said percutaneous lumen of said percutaneous fixation catheter substantially normal in relation to said catheter portion whereby said endoscope is stably fixed within the gastrointestinal lumen relative to the operating environment to thereby provide a stable platform for the performing of an endoscopic surgical procedure within the gastrointestinal lumen.

2. The stablized endoscope assembly of claim 1 in which said endoscope includes at least one articulated joint in the distal end portion of said endoscope.

3. The stabilized endoscope assembly of claim 2 wherein said endoscope includes at least one manipulator arm which is extensible from the distal end portion of said endoscope.

4. The stabilized endoscope assembly of claim 3 wherein said extensible manipulator arm includes an extensible rod attached to a helical spiral member.

5. An assembly for percutaneously stabilizing an endoscope positioned within a gastrointestinal lumen disposed within the abdominal wall and underneath the skin of a patient, said assembly comprising:

a fixation catheter having a distal tip portion, a proximal portion and a catheter portion, said catheter portion defining a catheter lumen extending said distal tip portion to said proximal portion, said catheter portion being percutaneously advanced through the skin, abdominal wall, and wall of the gastrointestinal lumen such that said distal tip portion is disposed within the gastrointestinal lumen;

a rigid mount, said rigid mount being fixed with respect to the operating environment;

means for fixedly attaching the endoscope relative to said rigid mount through said catheter lumen substantially perpendicular relative to said catheter portion whereby the endoscope is stably fixed within the gastrointestinal lumen relative to the operating environment to thereby provide a stable platform for the performing of an endoscopic surgical procedure within the gastrointestinal lumen.

6. The assembly of claim 5 wherein said attaching means includes a loop suture having a loop end disposed within the gastrointestinal lumen through said catheter lumen and a thread end remaining external to the patient.

7. The assembly of claim 6 wherein said attaching means includes a spool which is mounted in fixed relation to said rigid mount and wherein the thread end of said loop suture is tautly connected to said spool.

8. The assembly of claim 6 further comprising a collar which is slideably mounted on said loop suture.

9. The assembly of claim 5 wherein said proximal portion of said fixation catheter includes a skin bolster portion, said skin bolster portion including a plurality of holes extending therethrough.

10. The assembly of claim 5 wherein said proximal portion of said fixation catheter includes a skin bolster portion, at least a portion of said skin bolster being constructed of needle piercable material.

11. A stabilized endoscope assembly for anchoring an endoscope positioned within a gastrointestinal lumen disposed within the abdominal wall and underneath the skin of a patient, said assembly comprising:

an endoscope, said endoscope having a distal end portion disposed within the gastrointestinal lumen of a patient for the performing of an endoscopic surgical procedure therein;

a fixation catheter having a distal tip portion, a proximal portion and a catheter portion, said catheter portion defining a catheter lumen extending between said distal tip portion and said proximal portion, said catheter portion being percutaneously advanced through the skin, abdominal wall, and wall of the gastrointestinal lumen such that said distal tip portion is disposed within the gastrointestinal lumen;

a rigid mount, said rigid mount being fixed with respect to the operating environment; and a loop suture having a loop end disposed within the gastrointestinal lumen through said catheter lumen and encircling the circumference of said endoscope and a thread end tautly connected in fixed position relative to said rigid mount with said catheter portion of said fixation catheter fixed therebetween whereby said endoscope is stably fixed within the gastrointestinal lumen relative to the operating environment to thereby provide a stable platform for the performing of an endoscopic surgical procedure within the gastrointestinal lumen.

12. The stabilized endoscope assembly of claim 11 wherein said endoscope has a rigid section and wherein the loop end of said loop suture encircles said endoscope on said rigid section.

13. The stabilized endoscope assembly of claim 12 wherein said rigid section of said endoscope includes at least one annular groove and wherein the loop end of said loop suture lies in said groove.

14. The stabilised rindoscope assembly of claim 12 wherein said rigid section of said endoscope includes a series of alternating plateaus and grooves, each of said plateaus having a diameter which is greater than the minimum diameter of each of said grooves adjacent thereto, and wherein the loop end of said loop suture lies in one of said grooves in said rigid section of said endoscope.

15. The stabilized endoscope assembly of claim 12 wherein said rigid section of said endoscope includes a series of alternating hills and valleys, each of said hills having a maximum diameter which is greater than the minimum diameter of each valley adjacent thereto, and wherein the loop end of said loop suture lies in one of said valleys in said rigid section of said endoscope.

16. The stabilized endoscope assembly of claim 11 wherein said endoscope includes at least one articulated joint in the distal end portion of said endoscope.

17. The stabilized endoscope assembly of claim 16 wherein said endoscope includes at least one manipulator arm which is extensible from the distal end portion of said endoscope.

18. The stabilized endoscope assembly of claim 17 wherein said extensible manipulator arm includes an extensible rod attached to a helical spiral member.

19. The stabilized endoscope assembly of claim 18 wherein at least one of said manipulator arm(s) has a grasper connected thereto.

* * * * *

UNITED STATES PATENT AND TRADEMARK OFFICE
CERTIFICATE OF CORRECTION

PATENT NO. : 5,813,976
DATED : September 29, 1998
INVENTOR(S) : Charles J. Filipi; Douglas A. Comet It is certified that error appears in the above-identified patent and that said Letters Patent is hereby corrected as shown below:

In col. 1, line 30, "U.S" should begin a new paragraph.

In col. 1, line 30, please change "U.S" to --U.S.--.

In col. 6, line 4, please change "on" to --one--.

In col. 7, line 17, please change "angle" to --a wide--.

In col. 9, line 64, please change "endoscopic" to --endoscope--.

In col. 11, line 2, please change "piercable" to --pierceable--.

In col. 12, line 5, please change "stabilised rindoscope" to --stabilized endoscope--.

Signed and Sealed this

First Day of June, 1999

Attest:

Q. TODD DICKINSON

*Attesting Officer*     *Acting Commissioner of Patents and Trademarks*